United States Patent
Rout et al.

(10) Patent No.: US 11,839,360 B2
(45) Date of Patent: Dec. 12, 2023

(54) FLUOROPHORE IMAGING DEVICES, SYSTEMS, AND METHODS FOR AN ENDOSCOPIC PROCEDURE

(71) Applicants: Boston Scientific Scimed, Inc., Maple Grove, MN (US); The Johns Hopkins University, Baltimore, MD (US)

(72) Inventors: Sritam P. Rout, Lowell, MA (US); Marc Chelala, Baltimore, MD (US); Maria F. Torres, Baltimore, MD (US); Kyle R. Cowdrick, Baltimore, MD (US); Amir Hossein Soltanianzadeh, Baltimore, MD (US); David M. Gullotti, Baltimore, MD (US); Pankaj J. Pasricha, Ellicott City, MD (US); Nicholas J. Durr, Baltimore, MD (US); Ryan V. Wales, Northborough, MA (US)

(73) Assignees: Boston Scientific Scimed, Inc., Maple Grove, MN (US); The Johns Hopkins University, Baltimore, MD (US)

( * ) Notice: Subject to any disclaimer, the term of this patent is extended or adjusted under 35 U.S.C. 154(b) by 609 days.

(21) Appl. No.: 16/240,018

(22) Filed: Jan. 4, 2019

(65) Prior Publication Data
US 2019/0208997 A1 Jul. 11, 2019

Related U.S. Application Data

(60) Provisional application No. 62/614,266, filed on Jan. 5, 2018.

(51) Int. Cl.
*A61B 1/04* (2006.01)
*A61B 1/018* (2006.01)
(Continued)

(52) U.S. Cl.
CPC .......... *A61B 1/043* (2013.01); *A61B 1/00096* (2013.01); *A61B 1/00101* (2013.01);
(Continued)

(58) Field of Classification Search
CPC ..... A61B 1/043; A61B 1/018; A61B 1/00137; A61B 1/2736; A61B 1/00177;
(Continued)

(56) References Cited

U.S. PATENT DOCUMENTS 5,406,938 A * 4/1995 Mersch .............. A61B 1/00096
359/488.01
7,570,984 B2 8/2009 Katsuda et al.
(Continued)

FOREIGN PATENT DOCUMENTS

JP 4394402 B2 * 1/2010
JP 2011104333 A * 6/2011
(Continued)

OTHER PUBLICATIONS

Alander et al., A Review of Indocyanine Green Fluorescent Imaging in Surgery, 2012, Hindawi Publishing Corporation, International Journal of Biomedical Imaging vol. 2012, Article ID 940585, pp. 1-26 (Year: 2012).*

(Continued)

*Primary Examiner* — Aaron B Fairchild
*Assistant Examiner* — Stephen Floyd London
(74) *Attorney, Agent, or Firm* — Seager, Tufte & Wickhem, LLP (57) ABSTRACT

The present disclosure relates generally to fluorescent imaging devices, systems, and methods for an endoscopic procedure, and in particular, indocyanine green (ICG) fluorescence. In some embodiments, a device for fluorescent imaging during an endoscopic procedure may include an attachment connectable to a distal end of an endoscope. The (Continued)

attachment may include a first filter alignable with a light source of the endoscope, and a second filter alignable with an imaging device of the endoscope. The first filter may be positionable such that in a first position the first filter is aligned with the light source, and in a second position the first filter is out of alignment with the light source. The second filter may be positionable such that in a first position the second filter is aligned with the imaging device, and in a second position the second filter is out of alignment with the imaging device.

20 Claims, 4 Drawing Sheets

(51) Int. Cl.
| | | |
|---|---|---|
| *A61B 1/00* | (2006.01) | |
| *A61B 1/273* | (2006.01) | |
| *A61B 1/06* | (2006.01) | |
| *A61B 1/05* | (2006.01) | |
| *A61B 1/07* | (2006.01) | |

(52) U.S. Cl.
CPC ...... *A61B 1/00137* (2013.01); *A61B 1/00177* (2013.01); *A61B 1/00186* (2013.01); *A61B 1/018* (2013.01); *A61B 1/0646* (2013.01); *A61B 1/2736* (2013.01); *A61B 1/00165* (2013.01); *A61B 1/05* (2013.01); *A61B 1/0661* (2013.01); *A61B 1/07* (2013.01)

(58) Field of Classification Search
CPC ............ A61B 1/00101; A61B 1/00096; A61B 1/00186; A61B 1/0646; A61B 1/00165; A61B 1/05; A61B 1/07; A61B 1/0661; A61B 1/0008; A61B 1/00089; A61B 1/00098; A61B 1/00105; A61B 1/00135; A61B 1/00183; A61B 1/0615; A61B 1/0627; A61B 1/0014; G02B 7/006
USPC .......................................................... 600/175
See application file for complete search history.

(56) References Cited

U.S. PATENT DOCUMENTS

| | | | | |
|---|---|---|---|---|
| 2001/0049473 A1* | 12/2001 | Hayashi | ............ | A61B 1/00186 600/317 |
| 2005/0003323 A1* | 1/2005 | Katsuda | ............ | A61B 1/00101 433/29 |
| 2005/0065406 A1* | 3/2005 | Cline | ............ | A61B 1/0638 600/476 |
| 2006/0241499 A1* | 10/2006 | Irion | ............ | A61B 5/0071 600/476 |
| 2007/0142711 A1* | 6/2007 | Bayer | ............ | A61B 1/00177 600/172 |
| 2007/0177009 A1* | 8/2007 | Bayer | ............ | A61B 1/05 348/65 |
| 2008/0021274 A1 | 1/2008 | Bayer et al. | | |
| 2008/0027280 A1 | 1/2008 | Fengler et al. | | |
| 2008/0027286 A1* | 1/2008 | Xie | ............ | A61B 1/00096 600/181 |
| 2009/0173875 A1* | 7/2009 | Ichimura | ............ | A61B 1/00096 250/216 |
| 2011/0117025 A1 | 5/2011 | Dacosta et al. | | |
| 2012/0212595 A1* | 8/2012 | Parmar | ............ | A61B 5/0066 348/E7.085 |
| 2013/0034826 A1* | 2/2013 | Walsh | ............ | A61B 1/0607 433/29 |
| 2013/0211246 A1 | 8/2013 | Parasher | | |
| 2014/0343358 A1* | 11/2014 | Hameed | ............ | G02B 23/2423 600/109 |
| 2016/0062103 A1 | 3/2016 | Yang et al. | | |
| 2016/0154231 A1 | 6/2016 | Zhao et al. | | |
| 2016/0174814 A1 | 6/2016 | Igov | | |
| 2016/0212363 A1 | 7/2016 | Kim | | |
| 2017/0000314 A1* | 1/2017 | Honda | ............ | A61B 1/00052 |
| 2017/0235118 A1* | 8/2017 | Kuster | ............ | A61B 1/00186 600/476 |
| 2017/0258299 A1* | 9/2017 | Aikawa | ............ | A61B 1/00089 |
| 2018/0234603 A1 | 8/2018 | Moore et al. | | |
| 2019/0076007 A1* | 3/2019 | Higashiyama | ......... | A61B 1/046 |
| 2019/0208998 A1 | 7/2019 | Powers et al. | | |
| 2019/0246873 A1 | 8/2019 | Lu et al. | | |
| 2020/0352650 A1 | 11/2020 | Chu et al. | | |
| 2021/0022720 A1 | 1/2021 | Smith et al. | | |

FOREIGN PATENT DOCUMENTS

| | | |
|---|---|---|
| WO | 2006130730 A2 | 12/2006 |
| WO | 2008011722 A1 | 1/2008 |
| WO | 2009062179 A1 | 5/2009 |
| WO | 2018034075 A1 | 2/2018 |

OTHER PUBLICATIONS

International Search Report and Written Opinion for International Application No. PCT/US2019/012318, dated Jun. 17, 2019, 13 pages.
Buchs, Nicolas C., et al.,"Intra operative fluorescent cholangiography using indocyanin green during robotic single site cholecystectomy." The International Journal of Medical Robotics and Computer Assisted Surgery, 8(4): 436-440 (2012).
Ishizawa, T. et al., "Intraoperative Fluorescent Cholangiography Using Indocyanine Green: A Biliary Road Map for Safe Surgery." Journal of the American College of Surgeons, 208(1):e1-e4 (2009).
Author unknown, "Storz, Karl Sotrz—Endoskope" website [online], Mar. 2019 [retrieved on Mar. 4, 2019]. Retrieved from Internet URL: https://www.karlstorz.com/hk/en/fi.htm, 7 pages.
Figueiredo, JL, et al., "Intra-operative near-infrared fluorescent cholangiography (NIRFC) in mouse models of bile duct injury." World J Surg. 34(2): 336-343 (2010).
Scroggie, D. and Jones, C., "Fluorescent imaging of the biliary tract during laparoscopic cholecystectomy" Annals of Surgical Innovation and Research, 8(5): 1-6 (2014).

* cited by examiner

FLUOROPHORE IMAGING DEVICES, SYSTEMS, AND METHODS FOR AN ENDOSCOPIC PROCEDURE

CROSS-REFERENCE TO RELATED APPLICATIONS

This application is a non-provisional application of, and claims the benefit of priority to, U.S. Provisional Application Ser. No. 62/614,266, filed Jan. 5, 2018, entitled "Fluorophore Imaging Devices, Systems, and Methods for an Endoscopic Procedure," the entirety of which application is expressly incorporated by reference herein.

FIELD

The present disclosure relates generally to fluorophore imaging devices, systems, and methods for an endoscopic procedure, and more particularly for use of indocyanine green (ICG) to image the bile duct through the duodenum of a patient during an endoscopic retrograde cholangiopancreatography (ERCP) procedure.

BACKGROUND

In an endoscopic procedure, e.g., ERCP procedure, selective cannulation provides access to either the biliary duct or the pancreatic duct of a patient through the duodenal papilla. Orientation of the ducts may not be easily visualized by the medical professional, such that endoscopic tools may be incorrectly positioned and/or oriented. Cannulation may be difficult sometimes requiring a medical professional to make several attempts to access the biliary duct for therapeutic intervention, including, for example, exceeding a predefined time limit and/or exceeding a predefined number of unsuccessful attempts.

Contrast imaging may be used to visualize orientation of the ducts under fluoroscopy. However, the contrast is typically used only after cannulation, as the contrast agent is a known irritant of the ducts, and may place a patient at risk for post-ERCP pancreatitis.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a device for fluorescent imaging during an endoscopic procedure may include an attachment connectable to a distal end of an endoscope. The attachment may include a first filter alignable with a light source of the endoscope, and a second filter alignable with an imaging device of the endoscope.

In various of the foregoing and other embodiments of the present disclosure, the device for fluorescent imaging may be an indocyanine green (ICG) imaging device. The first filter may be positionable such that in a first position the first filter is aligned with the light source of the endoscope, and in a second position the first filter is out of alignment with the light source of the endoscope. The second filter may be positionable such that in a first position the second filter is aligned with the imaging device of the endoscope, and in a second position the second filter is out of alignment with the imaging device of the endoscope. The first filter may be an excitation filter for transmitting an excitation signal from the light source, to excite fluorophore of a fluorescent in an area of the endoscopic procedure. The second filter may be an emission filter for isolating light emitted by the fluorophore from light other than the light source as an emission signal. The first filter, or the second filter, or both, may be alignable with the respective light source and imaging device by a toggle mechanism. The toggle mechanism may be a mechanical toggle or an electrical toggle. The mechanical toggle may be a slide. The electrical toggle may be magnetically induced or voltage induced. The attachment may further include an opening for allowing an accessory device within a working channel of the endoscope to pass through the attachment. The attachment may further include an imaging sensor coupled to the second filter for enabling fluorescence imaging modality. The attachment may be a cap or a band.

According to an exemplary embodiment of the present disclosure, a fluorescent imaging system for an endoscopic procedure may include a light source, an excitation filter alignable with the light source, the excitation filter configured for transmitting a waveband of light as an excitation signal to excite fluorophore of a fluorescent in an area of the endoscopic procedure, an imaging device, and an emission filter alignable with the imaging device, the emission filter configured for isolating light emitted by the fluorophore from light other than the light source as an emission signal.

In various of the foregoing and other embodiments of the present disclosure, the fluorescent imaging system may be an indocyanine green (ICG) imaging system. The excitation filter may be positionable over the light source such that in a first position the excitation filter is aligned with the light source, and in a second position the excitation filter is out of alignment with the light source, and the emission filter may be positionable over the imaging device such that in a first position the emission filter is aligned with the imaging device, and in a second position the emission filter is out of alignment with the imaging device. The fluorescent imaging system may further include a mirror for separating the excitation signals and the emission signals. The excitation filter and the emission filter may be disposed on an attachment, the attachment being connectable to the light source, or the imaging device, or both. The light source, or the imaging device, or both, may be disposed on a duodenoscope. The fluorescent imaging system may be a remote imaging component and may be operatively connectable to a distal end of a duodenoscope within a body of a patient by fiber optic cables, such that the excitation signal, or the emission signal, or both, may be transferrable between the remote imaging component and the distal end of the duodenoscope by the fiber optic cables. The fluorescent imaging system may further include a fluorophore or phosphorescence coated guidewire, wherein the guidewire is visible by the fluorescent imaging system during the endoscopic procedure. Other types of instruments may be similarly coated.

According to an exemplary embodiment of the present disclosure, a method for imaging of an endoscopic procedure using fluorescent may include positioning a first filter relative to a light source, the first filter being configured for transmitting an excitation signal to excite fluorophore of a fluorescent in an area of the endoscopic procedure and positioning a second filter relative to an imaging device, the second filter being configured for isolating light emitted by the fluorophore from light other than the light source as an emission signal. The first filter may be positionable relative to the light source such that in a first position the first filter is aligned with the light source, and in a second position the first filter is out of alignment from the light source. The second filter may be positionable relative to the imaging device such that in a first position the second filter is aligned with the imaging device, and in a second position the second filter is out of alignment from the imaging device. The method for imaging of an endoscopic procedure may utilize indocyanine green (ICG) fluorescent.

In various of the foregoing and other embodiments of the present disclosure, the method may further include conducting fluorescence imaging when the first and second filter are in the first position and conducting visible light imaging when the first and second filter are in the second position.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

The devices, systems, and methods described herein are intended to overcome the disadvantages with using contrast imaging in an endoscopic, e.g., ERCP, procedure. For example, contrast is typically not injected into the biliary tree (including the pancreatic duct and biliary duct) until after cannulation is complete so as to reduce patient risk for pancreatitis. However, cannulation of the biliary or pancreatic duct may be difficult without being able to visualize and orient endoscopic tools to the duct.

In accordance with an exemplary embodiment of the disclosure, a fluorophore may be used instead to fluoresce desired regions in an endoscopic procedure, e.g., for purposes of cannulating the papilla to access the biliary and/or pancreatic ducts. In embodiments, devices, systems, and methods may utilize fluorophore for imaging in an endoscopic procedure as described herein and in co-pending application filed concurrently herewith, entitled "Fluorophore Imaging Devices, Systems, and Methods for an Endoscopic Procedure" to Powers et al., which is herein incorporated by reference in its entirety.

In some embodiments, indocyanine green (ICG) may be utilized, or another alternative fluorophore having characteristics similar to ICG (e.g., similar excitation and emission spectra), which may be injected intravenously, and secreted into bile. A fluorophore may be selected having characteristics similar to ICG at least partially based on near infrared (NIR) wavelengths. For example, lower wavelength spectra may have lower tissue penetration depth and lower signal-to-noise ratio due to tissue natural autofluorescence. Tissue autofluorescence may be particularly low in the NIR region, such that ICG (and other fluorophore having similar characteristics) may be desirable over other known fluorophores.

A fluorophore, such as ICG, may bind to plasma proteins, e.g., bile, upon which the protein bound fluorophore (e.g., ICG) may emit light. ICG, as an exemplary fluorophore, may be advantageous over known contrast imaging in that it may be injected into a patient intravenously, which is then excreted exclusively by the liver into bile. The ICG may be detectable within approximately 15 minutes of the injection, and may be present in the patient's system for detection for approximately two hours. As such, an injection of ICG may provide fluorescent images of a patient's biliary tract without necessitating gaining prior access to the bile duct. Near infrared (NIR) fluorescence imaging devices and systems in accordance with exemplary embodiments of the present disclosure may allow for fluorescence-based visualization of the ducts within a patient's biliary tree following an intravenous injection of fluorophore. For example, a medical professional may be able to visualize the orientation of a patient's bile duct on the duodenal wall, which may aide in orienting a sphincterotome or other endoscopic tool in the same direction.

Figure 1:
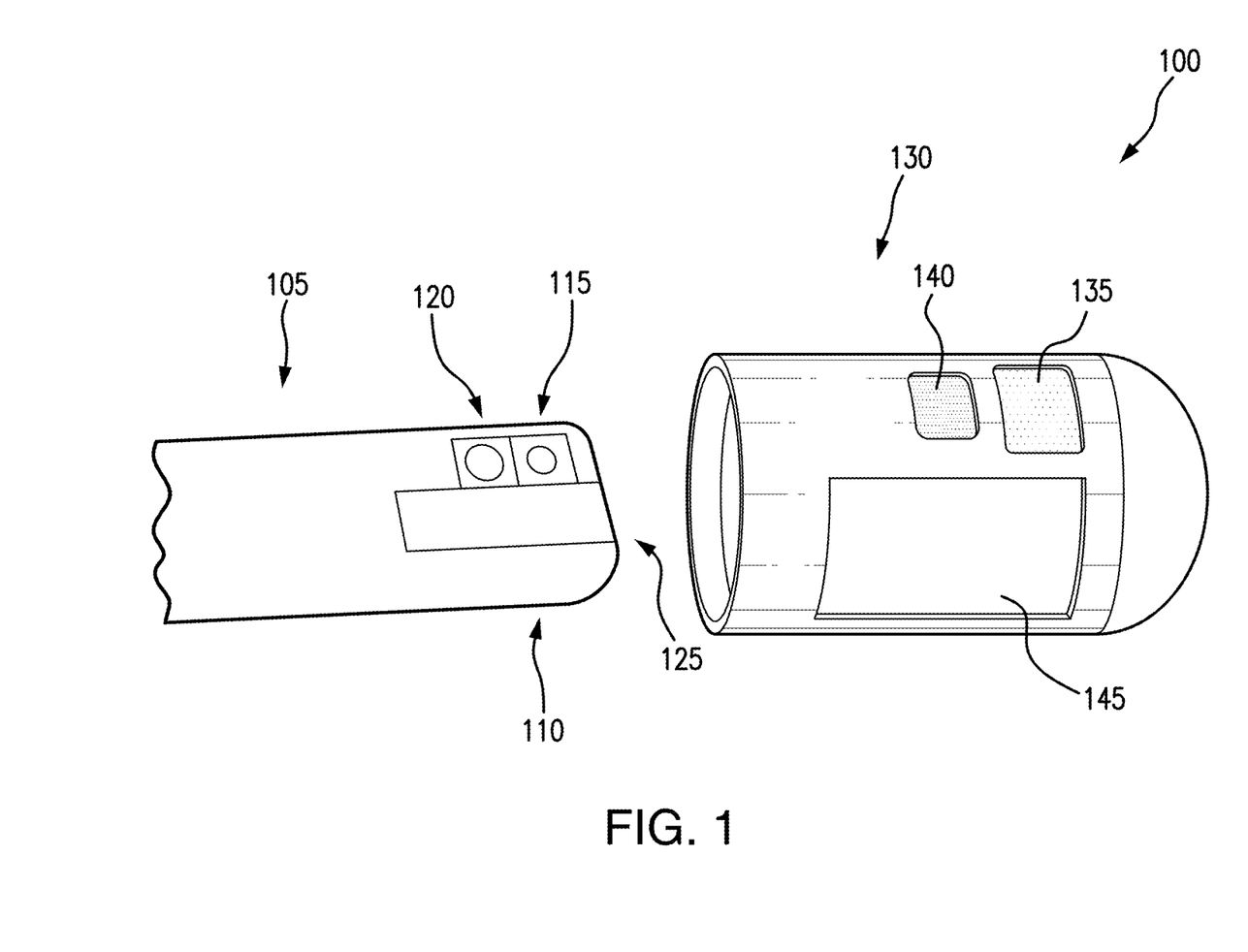
FIG. 1 illustrates an exemplary embodiment of a fluorescence imaging system and device in accordance with the present disclosure.
Figure 2A:
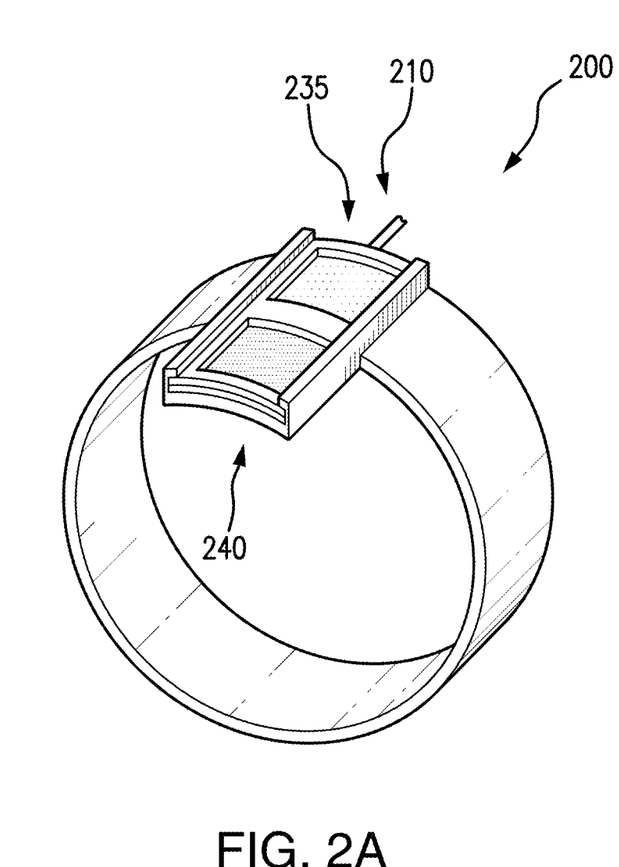
FIGS. 2A-2B illustrate another exemplary embodiment of a fluorescence imaging device in accordance with the present disclosure.
Figure 2B:
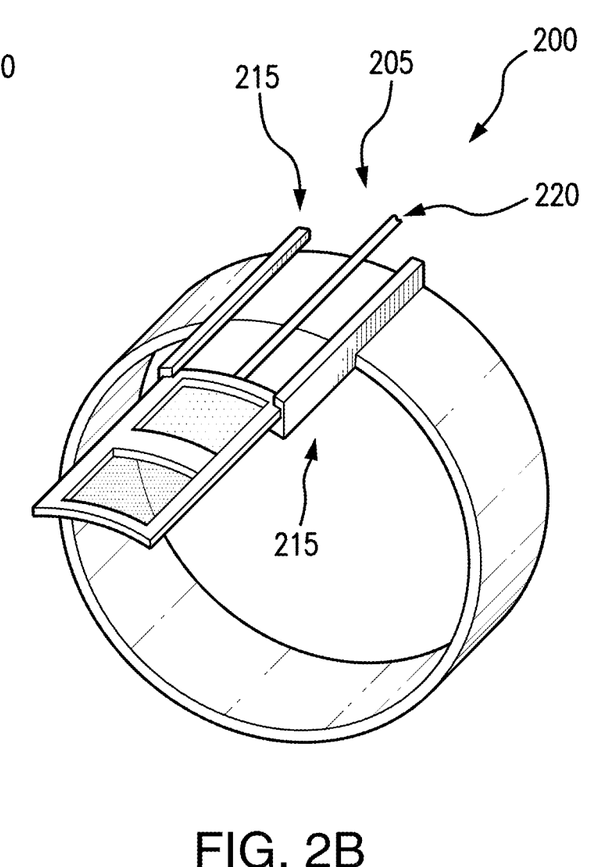

FIG. 1 illustrates an exemplary embodiment of a system 100 for fluorescent imaging (e.g., ICG fluorescence imaging) during an endoscopic procedure (e.g., ERCP procedure), and FIGS. 2A-2B illustrate another exemplary embodiment of a device 200 for fluorescent imaging (e.g., ICG fluorescence imaging) during an endoscopic procedure, e.g., for use in the system 100.

In an ERCP procedure, an endoscope, or duodenoscope 105, may be inserted into an intestinal region of a patient, e.g., into the duodenum of a patient adjacent biliary papilla. A distal end 110 of the duodenoscope 105 may include several accessories, for example, a light source 115 and an imaging device 120. In embodiments, the light source 115 may be a light emitting diode (LED), laser diode, or any method of emitting light that includes light at a 780 nm wavelength. In embodiments, the imaging device 120 may be a camera, or other detection system. The camera may have a non-zero quantum efficiency in the NIR region, e.g., equal to or greater than approximately 10%, in a waveband between approximately 800 nm and 850 nm. In embodiments, the camera may be a charge-coupled device (CCD) and/or complementary metal-oxide semiconductor (CMOS). The distal end 110 of the duodenoscope 105 may also include an elevator 125 so that a medical professional may manipulate additional accessory devices in the intestinal region of the patient at various angles to the shaft of the duodenoscope via the elevator 125.

As shown in FIG. 1, an attachment 130 may be removably connectable to the distal end 110 of the duodenoscope 105. The attachment 130 may include a first filter 135 and a second filter 140. When the attachment 130 is connected to the distal end 110 of the duodenoscope 105, the first filter 135 may be alignable with the light source 115, and the second filter 140 may be alignable with the imaging device 120. The attachment 130 may further include an opening 145, or accessory vent, alignable with the elevator 125, so that accessory devices extended from and retracted with a working channel of the duodenoscope 105 may pass through the opening 145. Although the system 100 shows the first filter 135 and the second filter 140, and the opening 145, on a side of the attachment 130 and adjacent each other, it is understood that the positioning of the first and second filters 135, 140, and the opening 145, may be anywhere on the attachment 130, including forward facing, to be alignable with the light source 115 and the imaging device 120 of an endoscope having front facing light source and imaging device components.

As shown in FIGS. 2A-2B, an attachment 200 may be removably connectable to the distal end 110 of the duodenoscope 105. The attachment 200 may include a first filter 235 and a second filter 240. When the attachment 200 is connected to the distal end 110 of the duodenoscope 105, the first filter 235 may be alignable with the light source 115, and the second filter 240 may be alignable with the imaging device 120. Although the attachment 200 shows the first filter 235 and the second filter 240 adjacent each other, it is understood that the positioning of the first and second filters 235, 240 may be anywhere on the attachment 200 to be alignable with the light source 115 and the imaging device 120 of the duodenoscope 105. In some embodiments, the attachment 200 may further include an opening (not shown), or accessory vent, alignable with the elevator 125, so that accessories extended from and retracted to the duodenoscope 105 may pass through the opening.

In some embodiments, the duodenoscope 105 may have an imaging device 120 that does not have adequate sensitivity in the NIR region, so that the attachment 130, 200 may include an additional imaging device (not shown) to enable the fluorescence imaging modality. For example, the additional imaging device may be a camera sensor, such as a CCD and/or CMOS. The additional imaging device may be coupled to the second filter 140, 240. In embodiments having an additional imaging device, the additional imaging device and the second filter 140, 240 may be positioned so as to not interfere with the imaging device 120 on the duodenoscope 105.

In embodiments, the first filter 135, 235 may be an excitation filter, and the second filter 140, 240 may be an emission filter. An excitation filter may be used to only transmit a narrow waveband from the light source 115 as an excitation signal, to excite fluorophore (e.g., of the ICG fluorescent) injected in or otherwise provided to an area of the endoscopic procedure. In embodiments, the waveband may be between approximately 760 nm and 790 nm. For example, an excitation filter may be a 769 nm center-wavelength bandpass filter, with 41 nm bandwidth and high transmission (e.g., up to approximately 90%) of light in the passing region, and high blocking outside the passing region (e.g., optical density approximately equal to or greater than 5). In embodiments, the first filter 135, 235, or excitation filter 140, 240, may be alignable with the light source 115 of the duodenoscope 105.

The second filter 140, 240, e.g., an emission filter, may be used to isolate light emitted by the fluorophore from light sources others than the light source 115 as an emission signal. In some embodiments, an emission filter for ICG imaging may transmit wavelength between approximately 810 nm and 840 nm. For example, an emission filter may be an 832 nm center-wavelength bandpass filter with 38 nm bandwidth and high transmission (e.g., up to approximately 90%) of light in the passing region, and high blocking outside of the passing region (e.g., optical density approximately equal to or greater than 5). In embodiments, the second filter 140, 240, or emission filter, may be alignable with the imaging device 120 of the duodenoscope 105.

The attachment 130, 200 may be installed and/or secured to the distal end 110 of the duodenoscope 105, so that the first filter 135, 235 and/or the second filter 140, 240 may be positionable relative to the light source 115 and the imaging device 120, respectively. For example, the attachment 130, 200 may be a cap (FIG. 1), or a band (FIGS. 2A-2B), or any other configuration for attachment to an external surface of the duodenoscope 105. The attachment 130, 200 may alternatively or additionally be connectable to the to an internal surface of the duodenoscope 105, e.g., via the elevator 125. In some embodiments, the attachment 130, 200 may be movable relative to the distal end 110 of the duodenoscope 105. In other embodiments, the attachment 130, 200 may be fixed to the distal end 110 of the duodenoscope 105, with the first filter 135, 235 and/or the second filter 140, 240 being movable relative to the attachment 130, 200.

During an endoscopic procedure, e.g., an ERCP procedure, an endoscope, or a duodenoscope 105, may be inserted into a patient, e.g., through a patient's mouth through the stomach and into the duodenum. The endoscope may be positioned along the duodenal wall at the biliary tree, and fluorescent (e.g., ICG fluorescent) may be provided to the area for imaging. In embodiments, the fluorescent may be provided before or after, or simultaneous, to the endoscope being inserted into the patient. The fluorescent may need time, e.g., approximately 15 minutes for ICG fluorescent, to bind to bile to fluoresce during the procedure. When the endoscope is in position and the fluorescent has had sufficient binding time, a medical professional may manipulate a distal end of the endoscope. For example, the endoscope may be positioned so that a light source, or an imaging device, or both, allow a medical professional to view the bile duct at the duodenal wall. According to exemplary embodiments of the present disclosure, filters may be alignable with the light source, or the imaging device, or both, so that the medical professional may view the area under white light, as well as filtered (e.g., under fluorescence). For example, the first filter 135, 235, or excitation filter, may be alignable with the light source, and the second filter 140, 240, or emission filter, may be alignable with the imaging device 120. The medical professional may be able to toggle between white light and filtered imaging as desired. Under white light, the filters may not be used, so that the medical professional may view the area as illuminated by the light source (see FIG. 4A). When filtered, the contrast (e.g., ICG fluorescent) in the area may fluoresce, illuminating a path of the ducts (e.g., the bile duct), so that the medical professional may guide an accessory device (e.g., a guidewire) into the duct (see FIG. 4B). When the duct is illuminated by the fluorescent (e.g., ICG fluorescent), the medical professional may have a clear view of a path for cannulation.

In embodiments, a method for imaging an endoscopic procedure (e.g., during an ERCP procedure) may include positioning the first filter 135, 235 relative to the light source 115, and positioning the second filter 140, 240 relative to the imaging device 120. The fluorescent imaging system 100, 300 (e.g., an ICG fluorescence imaging system) (see FIGS. 3A-3B) may allow a medical professional to efficiently cannulate and verify proper access into a patient's biliary and/or pancreatic during an ERCP procedure. For example, the first filter 135, 235 may be positionable such that in a first position 205 the first filter 135, 235 is aligned with the light source 115 of the distal end 110 of the duodenoscope 105 (see FIG. 2A). In a second position 210, the first filter 135, 235 may be out of alignment from the light source 115 of the distal end 110 of the duodenoscope 105 (see FIG. 2B). Similarly, the second filter 140, 240 may be positionable such that in a first position 205 the second filter 140, 240 is aligned with the imaging device 120 of the distal end 110 of the duodenoscope 105 (see FIG. 2A). In a second position 210, the second filter 140, 240 may be out of alignment from the imaging device 120 of the distal end 110 of the duodenoscope 105 (see FIG. 2B). It may be advantageous for the first filter 135, 235 and/or the second filter 140, 240 to be positionable so that a medical professional may view an area by the imaging device 120 and/or illuminate an area by the light source 115 with and without fluorescence.

In some embodiments, the attachment 130, 200 may include a toggle mechanism for moving the first filter 135, 235 and/or the second filter 140, 240 in and out of alignment with the light source 115 and/or imaging device 120, respectively. For example, the toggle mechanism may be a mechanical toggle. As shown in FIGS. 2A-2B, the first and second filter 235, 240 may be disposed within slide channels 215 and connected to a pusher 220. The pusher 220 may be a wire, manipulatable by a user manually or automatically for moving the first and second filter 135, 235, 140, 240 in and out of alignment as a slide, e.g., sliding the first and second filters 135, 235, 140, 240 along the slide channels 215. Although FIGS. 2A-2B show the slide channels 215 and pusher 220 movable in a longitudinal direction, e.g., along a longitudinal axis of a duodenoscope, it is understood that a toggle mechanism may allow the first and second filters 135, 235, 140, 240 to be movable in any linear and/or rotational direction.

In some embodiments, the toggle mechanism may be an electrical toggle. An electrical toggle may be magnetically induced, voltage induced, or another electrical mechanism for switching between "on" (e.g., aligning the first and/or second filters 135, 235, 140, 240 to the light source 115 and imaging device 120, respectively), and "off" (e.g., moving the first and/or second filters 135, 235, 140, 240 out of alignment from the light source 115 and imaging device 120, respectively). It is understood that the user, or medical professional, may have control over the electrical toggle, to switch between white-light imaging and NIR fluorescence imaging during an endoscopic procedure, such as an ERCP procedure.

Figures 3A, 3B:
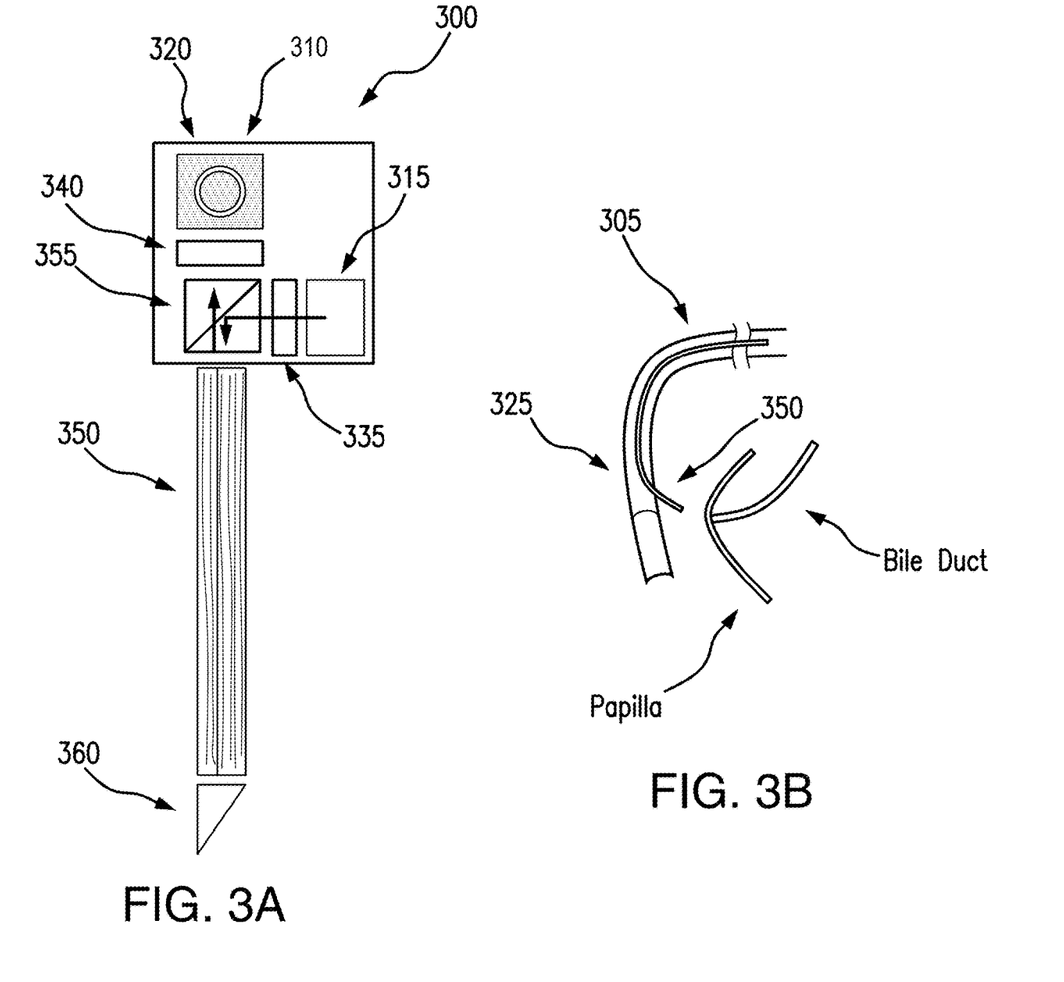
FIGS. 3A-3B illustrate another exemplary embodiment of a fluorescence imaging system in accordance with the present disclosure.

Referring now to FIGS. 3A-3B, another exemplary embodiment of a fluorescence imaging system (e.g., an ICG fluorescence imaging system) in accordance with the present disclosure is shown. A fluorescence imaging system (e.g., ICG fluorescence imaging system 300) may be disposed outside of the patient, with optical signals being transferred via fiber optic cables or bundles. For example, a remote imaging component 310 may include a light source 315, a first filter 335 (e.g., an excitation filter), an imaging device 320, and a second filter 340 (e.g., an emission filter), and may be disposed remotely from the patient. A fiber optic cable 350, or bundles, may be connectable to the remote imaging component 310, and extendable a length for insertion through a duodenoscope, e.g., duodenoscope 105, 305. In this manner, the imaging system 300 may allow a medical professional to efficiently cannulate and verify proper access during an endoscopic procedure, such as an ERCP procedure.

The fiber optic cable 350 may be a single cable, or a plurality of cables, or bundles of cables. In some embodiments, the fiber optic cable may be a single-mode or a multi-mode, comprised of a single core or multiple cores. In some embodiments, the fiber optic cable may be already-present in the duodenoscope 105, 305 used for the light source 115 and/or conveying images to a remote imaging device 120, or embodied in existing accessories, such as a sphincterotome or cannula, or through a scope-in-scope system (e.g., a cholangioscope). In other embodiments, the fiber optic cable may be separate from any accompanying cables of the light source 115 and/or imaging device 120. As a separate cable, the fiber optic cable 350 may be extended into and retracted from a patient via the elevator 125, 325 of the duodenoscope 105, 305, for visualization of an accessory device, such as a guidewire (not shown), being inserted into the bile duct. In some embodiments, the fiber optic cable 350 may be mounted externally on the duodenoscope 105, 305 using fasteners, including but not limited to mechanical fasteners, accessory clips, wires, ties, and the like.

In some embodiments, the remote imaging component 310 may further include a mirror 355. For example, using fiber optic cable 355 may result in excitation signals and emission signals being transferred between the remote imaging component 310 and a distal end of the duodenoscope or other device through the same channel. A mirror 355, such as a dichroic mirror, may separate the excitation signals and the emission signals. In some embodiments, a prism 360 may be disposed at a distal end of the fiber optic cable 350, for redirecting a field of view in the patient. In some embodiments, the assembly of the dichroic mirror may be mounted at approximately 45 degrees to the first filter 335 (e.g., the excitation filter) and second filter 340 (e.g., the emission filter), which may be incorporated as a filter cube and/or an objective lens. In some embodiments, image magnification may be desirable, which may be achieved by utilizing a fiber optic taper and/or an objective lens.

Figure 4A:
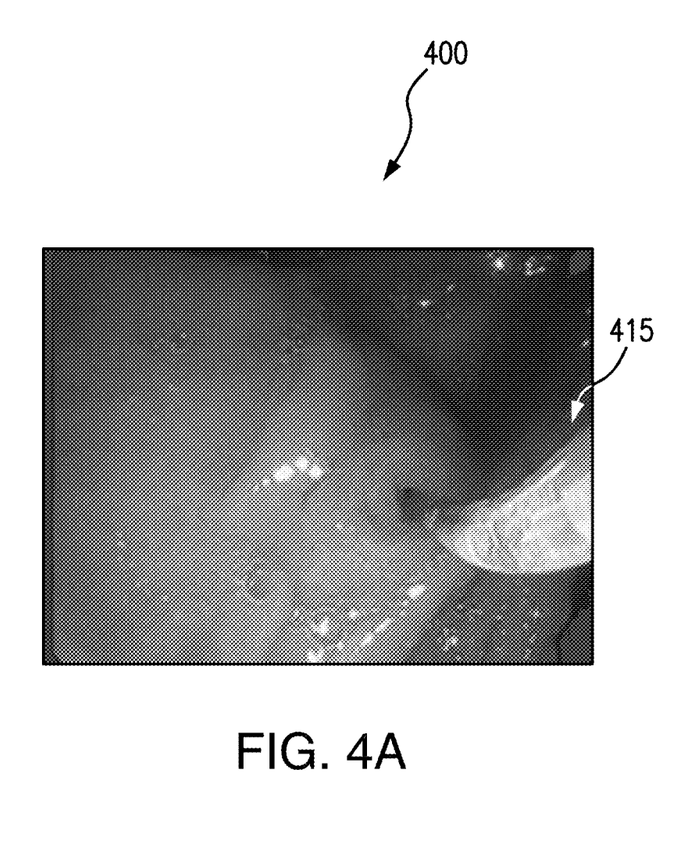
FIG. 4A illustrates a duodenum wall and bile duct under white light in accordance with an exemplary embodiment of the present disclosure.
Figure 4B:
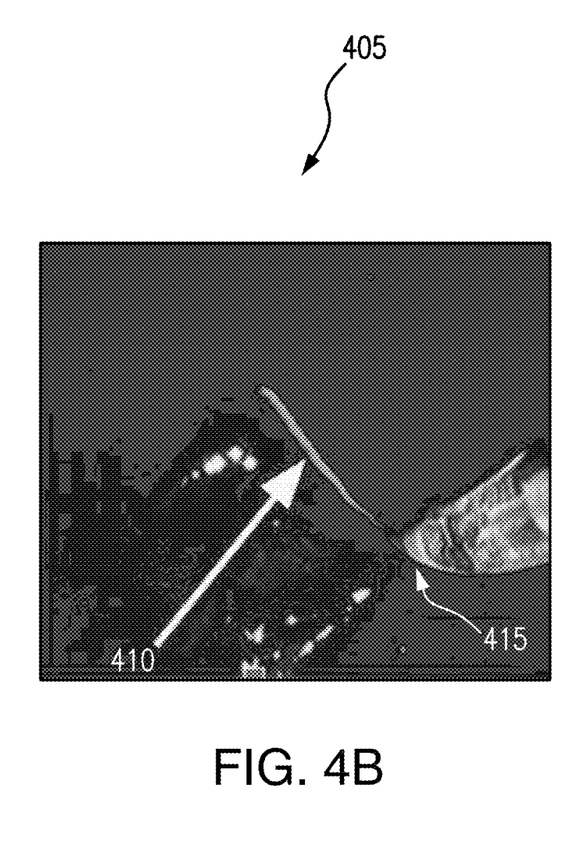
FIG. 4B illustrates a duodenum wall and bile duct under fluorescence in accordance with an exemplary embodiment of the present disclosure.

As described above, the fluorophore (e.g., ICG fluorescent) may be injected into a patient to allow for the biliary and/or pancreatic duct to be visible by a medical professional when filtering the light by the first and/or second filters 135, 235, 140, 240. As shown in FIGS. 4A-4B, the duodenum may be visible under white light at 400 (FIG. 4A), and the bile duct may be visible through a filtered image 405 by the fluorescence (e.g., ICG fluorescent) and the first and/or second filter 135, 235, 140, 240, so that the medical professional may visualize the orientation of the bile duct (indicated by reference numeral 410) for insertion of the guidewire during the ERCP procedure (FIG. 4B). As shown in FIGS. 4A-4B, this visualization may allow a medical professional to position a sphincterotome or cannula 415 for accessing the bile duct. The cannula 415 may include one or multiple channels for a guidewire for insertion and/or to inject contrast.

In some embodiments, a guidewire or other accessory device may also be at least partially coated in a fluorophore or phosphorescent material. For example, a tip of a guidewire, e.g., a flexible tip, may be coated up to approximately 10 cm with a fluorophore or phosphorescent material having a similar emission wavelength as ICG. The coating may have a larger quantity located on the guidewire tip, and therefore have a higher intensity to what fluoresces in the ducts. This may allow the medical professional to locate the guidewire easily in the filtered image. In some embodiments, the coating on the guidewire may have a wavelength unique to itself, allowing for detection of the guidewire independent from detection of the ducts, relative to ICG. The wavelength may only be slightly different from ICG, so that the same first and second filters 135, 235, 140, 240 may be utilized for visualizing both the guidewire and bile duct. In other embodiments, the wavelength may be significantly different from ICG, which may necessitate additional filters (e.g., excitation and emission filters), so that the medical professional may toggle between viewing the bile duct and viewing the guidewire.

In some embodiments (e.g., to eliminate toggling), images of the ducts and the guidewire may be interlaced and/or superimposed, to provide simultaneous visualization of the ducts and the guidewire. For example, fluorescence and white light imaging may be both visible to facilitate visualization of both the trajectory of the guidewire and the anatomical features (e.g., the papilla). In some embodiments, a coated guidewire may be used without prior fluorophore (e.g., ICG) injection. Although the medical professional may visualize the guidewire in the filtered image, the bile duct will not be outlined by fluorescence. Other devices may be similarly coated and visualized/imaged.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A device for fluorescent imaging during an endoscopic procedure, comprising:
   an attachment connectable to a distal end of an endoscope, the attachment including:
   a tubular body;
   a first filter disposed along the tubular body, the first filter alignable with a light source of the endoscope; and
   a second filter disposed along the tubular body, the second filter alignable with an imaging device of the endoscope,
   wherein at least one of the first and second filters are movable, within a patient and during use, along a longitudinal axis of the tubular body relative to the tubular body between a first position and a second position.

2. The device of claim 1, wherein the first filter is movable, within the patient, along the longitudinal axis of the tubular body such that in the first position the first filter is aligned with the light source of the endoscope, and in the second position the first filter is out of alignment with the light source of the endoscope.

3. The device of claim 1, wherein the second filter is movable, within the patient, along the longitudinal axis of the tubular body such that in the first position the second filter is aligned with the imaging device of the endoscope, and in the second position the second filter is out of alignment with the imaging device of the endoscope.

4. The device of claim 1, wherein the first filter is an excitation filter for transmitting an excitation signal from the light source, to excite a fluorophore of a fluorescent in an area of the endoscopic procedure.

5. The device of claim 4, wherein the second filter is an emission filter for isolating light emitted by the fluorophore, from light other than the light source, as an emission signal.

6. The device of claim 1, comprising a toggle mechanism configured to move the at least one of the first and second filters between the first position and the second position.

7. The device of claim 6, wherein the toggle mechanism is a mechanical toggle or an electrical toggle.

8. The device of claim 7, wherein the mechanical toggle is a slide.

9. The device of claim 7, wherein the electrical toggle is magnetically induced, or voltage induced.

10. The device of claim 1, wherein the attachment further includes an imaging sensor coupled to the second filter for enabling fluorescence imaging modality, and wherein the attachment is a cap or a band.

11. The device of claim 1, wherein the fluorescent imaging is indocyanine green (ICG) fluorescent imaging.

12. An attachment for an endoscope, comprising:
    a tubular body comprising a proximal end and a distal end;
    a first filter disposed along the tubular body;
    a second filter disposed along the tubular body and proximal of the first filter, wherein at least one of the first and second filters are movable, within a patient and during use, along a longitudinal axis of the tubular body relative to the tubular body; and an aperture disposed along the tubular body and circumferentially adjacent the first filter.

13. The attachment of claim 12, wherein the distal end of the tubular body comprises a closed cap.

14. The attachment of claim 12, wherein a surface of each of the first filter and the second filter comprises a curved surface.

15. The attachment of claim 12, wherein the first filter is alignable with a light source of the endoscope and wherein the second filter is alignable with an imaging device of the endoscope.

16. The attachment of claim 12, wherein the aperture is alignable with a channel of the endoscope.

17. A system for fluorescent imaging during an endoscopic procedure, comprising:

an endoscope comprising a distal end and a side facing imaging device;

an attachment removable from about the distal end of the endoscope, the attachment comprising:

a tubular body;

a first filter disposed along the tubular body;

a second filter disposed along the tubular body, the second filter alignable with the side facing imaging device of the endoscope, wherein at least one of the first and second filters are movable, within a patient and during use, along a longitudinal axis of the tubular body relative to the tubular body; and an aperture disposed along the tubular body and circumferentially adjacent the first filter.

18. The system of claim 17, wherein the first filter is alignable with a light source of the endoscope.

19. The system of claim 17, wherein the aperture is alignable with a channel of the endoscope.

20. The system of claim 17, wherein a surface of each of the first filter and the second filter comprises a curved surface.

* * * * *